(12) United States Patent
Dudich et al.

(10) Patent No.: US 7,446,095 B2
(45) Date of Patent: Nov. 4, 2008

(54) PEPTIDES MODULATING CASPASE ACTIVATION

(76) Inventors: Elena Ivanovna Dudich, Sprotivnaya u. 11-55, Lyubuchany, Moscow Region (RU) RU-142380; Lidia Nikolaevna Semenkova, Sprotivnaya Ul. 13-24, Lyubuchany, Moscow Region (RU) RU-142380; Igor Vyacheslavovitch Dudich, Sprotivnaya u. 11-55, Lyubuchany, Moscow Region (RU) RU-142380; Edvward Borisovitch Tatulov, Aviatorov ul 8/1-148, Moscow (RU) RU-119619; Dimitry Lvovicth Zubov, 1st Goncharny pr. 7-42, Moscow (RU) RU-11572; Timo Kalevi Korpela, Kraatarinkatu 1 D 42, Turku (FI) FIN-20610

( * ) Notice: Subject to any disclaimer, the term of this patent is extended or adjusted under 35 U.S.C. 154(b) by 323 days.

(21) Appl. No.: 10/530,779

(22) PCT Filed: Oct. 7, 2003

(86) PCT No.: PCT/FI03/00735

§ 371 (c)(1),
(2), (4) Date: Apr. 8, 2005

(87) PCT Pub. No.: WO2004/033500

PCT Pub. Date: Apr. 22, 2004

(65) Prior Publication Data

US 2006/0280732 A1    Dec. 14, 2006

(30) Foreign Application Priority Data

Oct. 9, 2002  (FI)  ................................. 20021798

(51) Int. Cl.
| | |
|---|---|
| A61K 38/04 | (2006.01) |
| A61K 38/08 | (2006.01) |
| A61K 38/10 | (2006.01) |
| A61K 38/12 | (2006.01) |
| C07K 7/00 | (2006.01) |
| C07K 7/06 | (2006.01) |
| C07K 7/08 | (2006.01) |
| C07K 7/64 | (2006.01) |

(52) U.S. Cl. .................. 514/15; 514/2; 514/9; 514/13; 530/317; 530/326; 530/328; 530/387.2; 424/131.1

(58) Field of Classification Search .................. None
See application file for complete search history.

(56) References Cited

FOREIGN PATENT DOCUMENTS

| EP | 0353814 | 2/1990 |
|---|---|---|
| WO | WO96/22787 | 8/1996 |
| WO | WO98/10787 | 9/1997 |
| WO | WO98/35981 | 8/1998 |
| WO | WO01/15709 | 3/2001 |
| WO | WO03/007978 | 1/2003 |

OTHER PUBLICATIONS

Rudinger J, Characteriistics of the amino acids as components of a peptide hormone sequence, Peptide Hormones, JA Parsons, Edition, 1976, 1-7.*
Designing Custom Peptides from SIGMA, Dec. 16, 2004 web access, 1-2.*
Berendsen HJC, A Glimpse of the Holy Grail?, Science, 1998, 282: 642-643.*
Voet D and Voet JG, Biochemistry, 2nd Edition, John Wiley & Sons, Inc., 1995, 235-241.*
Bennet et al. 2001: A petide derived from alpha fetoprotein prevents . . . PNAS vol. 99; No. 4. 2211-2215.
Dudich I. et al 1999. Isolation and Structural and Functional Characterization . . . Biochemistry 38:10406-10414.
Buckley et al. 1999. RGD peptides induce apoptosis by direct caspase . . . Nature vol. 397 p. 534-539.
Bratton S. B et al. 2001. Recruitment, activation and retention of . . . The EMBO Journal 20. No. 5. pp. 998-1009.
Cohen G. M. 1997. Caspase: the executionres of apoptosis. Biochem J. 326: 1-16.
Dudich E. et al. 1999 Alpha Fetprotein causes apoptosis in tumor . . . Eur. J. Biochem. 266, 750-761.
Semenkova L. et al. 2003. Alpha Fetoproein positively regulates cytochrome Eur. J. Biochem 270: 4388-4399.
Maccoll et al. 2001. Interrelationships among biological activity, disulfide . . . Biochimica et Biophyscia Acta 1528: 127-134.
Morinaga T. et al. 1983. Primary structures of human alpha fetoprotein . . . Proc. Natl. Acad. Sci USA vol. 80 pp. 4604-4608.
Nagata S. 1997. Apoptosis by Death Factor. Cell 88:355-365.
Pasqualini, R. et al. 1995. A peptide isolated form phage display . . . The Journal of Cell Biology. vol. 130: 5 pp. 1189-1196.

* cited by examiner

*Primary Examiner*—Anish Gupta
*Assistant Examiner*—Julie Ha
(74) *Attorney, Agent, or Firm*—Dodds and Associates; John Dodds; Susanne Somersalo (57) ABSTRACT

The present invention provides structures of small molecules capable of modulating apoptotic cell death. More specifically, the structures relate to the structures of apoptotic active sites of mammalian alpha-fetoprotein (AFP) and albumin. Peptides mimicking the active site contain two sequences, Arg-Gly-Asp and Asp-X-X-Asp, wherein X means any amino acid. These sequences are needed in the same molecule for causing a wide range of biological activities. The peptides can be utilized to suppress apoptotic pathways by inhibiting the cytochrome c-mediated caspase activation. Thus, the peptides can be used to inhibit effects of apoptosis induced by oxidative stress, drugs, cytokines, Fas-ligand, alpha-fetoprotein, used to prevent apoptosis in culturing cells, in organ transplantation, in immunological autoimmune disorders and immunodeficiency syndrome induced by viral infection, or to diminish side cytotoxic effects after chemotherapy and radiation therapy.

7 Claims, 9 Drawing Sheets

Fig.7 A and B

PEPTIDES MODULATING CASPASE ACTIVATION

This is national stage application under 35 U.S.C. section 371 of international application PCT/FI2003/000735 filed on Oct. 7, 2003 said international application claiming priority of the Finnish national patent application F120021798 filed on Oct. 9, 2002.

SEQUENCE DATA

This application contains sequence data provided on a computer readable diskette and as a paper version. The paper version of the sequence data is identical to the data provided on the diskette.

FIELD OF THE INVENTION

The present invention is related to medicine and mechanisms of death of human and animal cells. In particular, it is related to peptides capable of inhibiting apoptotic cell death induced by different factors. The invention describes peptides with such activities and methods of producing and using said peptides.

BACKGROUND OF THE INVENTION

Apoptosis is an active form of cell death that is involved in multiple processes of normal cell development as well as in malignant cell transformations. Mechanism of apoptosis is engaged in biological events induced by various types of drugs, cytokines, and growth factors, oxidative stress, radiation, aging, autoimmune diseases, and immune rejection within organ transplantation. Recent studies on apoptosis demonstrate that common molecular mechanisms are employed in various types of apoptosis, induced by hormones, cytokines, growth factor deprivation, chemotherapeutic agents, ionizing radiation, immunological disorders, AIDS, cancer and aging (Nagata, (1997) *Cell* 88, 355-365).

Cascade-like activation of caspase proteases represents the fundamental point in the induction of apoptosis. Two distinct types of apoptosis signaling are described. The initial phase of receptor-depending triggering of apoptosis includes activation of appropriate death receptors by specific ligands, such as TNF or FasL, which are presently the most studied inductors of apoptosis. Upon activation, cell surface death receptors, Fas (CD95) or TNFR1, are attached to cytosolic adapter proteins (FADD, MORT, RIP, TRADD), which in turn recruit caspase-8 to activate the interleukin-1-β-converting enzyme ICE/CED-3 family protease (caspase) cascade, followed by activation of CPP32/caspase-3-subfamily of cysteine proteases, whose members occur in cell cytoplasm in the form of latent precursors, procaspases. Receptor-independent types of apoptosis usually include critically important cytochrome c-inducible mechanism that requires the formation of tertiary complex of cytochrome c, dATP, Apaf-1 and procaspase-9, that lead to the activation of the latter via autoproteolysis and homodimerization, and subsequent caspase cascade activation (Cohen et al. 1997 Biochem. J. 326: 1-16.).

Agents that affect the biological control of apoptosis thus have a potential therapeutic utility in numerous clinical applications. A variety of plant-derived inhibitors of apoptosis are employed to screen pathological disorders that often accompany chemotherapy, radiation, immune disorders, or AIDS. These supplements generally contain carbohydrates, fat and plant protein hydrolysates, lectins, and phospholipids (U.S. Pat. No. 6,004,579, Barr et al.). Potent regulators of apoptosis could be employed in the treatment of cancer patients to control cytokine therapy, chemotherapy, or radiation therapy. Apoptotic mechanisms operate at the various types of immunological disorders, such as autoimmune malignancies, immune rejection in organ transplantation or anaphylaxis, or viral infections with human immunodeficiency virus.

Alpha-fetoprotein (AFP) is a tumor-associated fetal glycoprotein displaying a wide range of biological activities, including cell growth regulation, differentiation of immature cells, immunosuppression of activated immune cells, tumor-specific induction of apoptosis and regulation of apoptotic signals mediated by other factors, as well as regulation of various gene expressions (Mizejewski, (2001). *Exp. Biol. Med.*, 226: 377-408). Multiple evidences of cell growth regulative activities, including tumor suppressive activity, have been reported for various species of full-length AFP molecule , its proteolytic fragments or recombinant domains and synthetic peptides (Dudich et al. 1999, Biochemistry 38: 10406-104141; MacColl et al. 2001 Biochim. Biophys. Acta, 1528: 127-134). The search for the localization of functional active sites of the AFP molecule which are responsible for its multiple activities has been undertaken by various researchers. Localization of the arachidonic acid and estradiol binding sites have been successful (reviewed at Mizejewski, (2001). *Exp. Biol. Med.*, 226: 377-408).

It was demonstrated recently, that AFP realizes its tumor-suppressive activity by triggering apoptosis through activation of caspase-3 and independently on Fas/FasL and TNF/TNFR signaling (Dudich et al., (1999) *Eur. J Biochem.* 266: 1-13; Semenkova et al., (1997) *Tumor Biology,* 18: 261-274; Dudich et al. (1998) *Tumor Biology,* 19:30-40). Multiple evidences of the AFP-mediated tumor cell growth suppression have been reported at the last decade, but the active site of the AFP molecule that is responsible for apoptosis signaling has not been identified. DNA and amino acid sequences of human AFP have been reported (Morinaga, et.al., "Primary structures of human alpha-fetoprotein and its mRNA" *Proc. Natl. Acad. Sci. USA,* 80:4604-4608 (1983). Synthetic peptides, corresponding to the E2-binding site were shown to possess tumor-suppressive activity (U.S. Pat. No. 5,674,842; October 1997 Mizejewsky; U.S. Pat. No. 5,707,963, July 1998 Mizejewsky). Variety of biologically active proteins shares a sequence homology with AFP (Mizejewski, (2001) Exp. Biol. Med. 226: 377-408). There has been identified authentic homology of AFP with various proteins, involved in apoptosis signaling, such as Bcl2, TNFR1, Fas, etc. (Mizejewski, (2001). WO9835981 A1 (Economou, J. et al. 1998) describes using of 66 AFP peptide sequences to be useful for immunization against cancer. One of the peptides, A20, was CRGD-VLDCL, which incidentally happens to include a part of the active site of AFP, found in the present disclosure. However, no special effects by the peptide CRGDVLDCL were found and the present invention remains to be the first one able to identify one of the putative biologically active sites of AFP. Moreover, the peptides of the present invention include an additional cysteine residue which enables the formation of inter-chain disulphide bonds and to produce a significantly higher biological activity than the sequence CRGDVLDCL.

An important integrin binding site is a tripeptide Arg-Gly-Asp, which is present in a variety of intergrin ligands. Integrins are hetorodimeric glycoproteins mediating cell-matrix and cell-cell interactions and have an active role in the processes of cell differentiation, immune recognition, tumor development and metastatic growth. Contact regions for the Arg-Gly-Asp sequence have been identified in the integrin subunits (see Pasqualini, et al. *J. Cell Biol.* (1995)130: 1189-1196). Synthetic peptides containing the Arg-Gly-Asp motif are used as inhibitors of integrin-ligand interactions. It has been reported that synthetic peptides containing Arg-Gly-Asp motif are able of direct caspase-3 activation (Bukley, et al. (1999) *Nature*, 397: 534-539). AFP contains Arg-Gly-Asp (RGD) sequence in its sequence that it localized in the domain II in the position 253-255. According to the present invention, the RGD sequence is a part of the functionally active site of AFP involved in the apoptosis signaling.

The present invention describes the minimal part of the AFP molecule that is responsible for the apoptosis signaling. Small peptides or other small haptens are important regulators to be used as the drugs because they can be synthesized in vitro and they do not produce neutralizing antibodies. Peptides containing from 6 to 10 residues were produced with the aid of the F-MOC solid phase chemistry. The similar peptides corresponding to homologous sequences of human serum albumin (HSA) were also synthesized. All peptides were assessed for their growth regulative activity in whole cells in culture and also tested for their ability to directly induce caspase activation in cell-free cytosolic extracts. Additionally, the peptides were assessed for their ability to modulate apoptosis induced by AFP and anti-Fas cytotoxic Mabs CH-11 in whole cells and to affect cytochrome c-induced caspase activation in cell-free systems.

BRIEF DESCRIPTION OF THE DRAWINGS

FIG. 7 shows the synergistic enhancement of the cytochrome c-mediated caspase activation in a cell-free system with human AFP. (A) AFP induces caspase-3 activation in cell-free cytosolic extracts in the presence of dATP. Aliquots of HepG2-derived cytosolic extract (25 μg of protein) were treated for various time intervals with AFP (7 μM) or as a control with the same dose of HSA in the presence of dATP (1 mM) and then assayed for DEVDase activity. (B) Synergistic enhancement of the caspase-3 activation mediated by AFP in the presence of the suboptimal dose of exogenous cytochrome c in cytosolic extracts of HepG2 cells. Aliquots of the HepG2-derived cytosolic extract (25 μg of protein) were treated for various time intervals with AFP (10 μM), cytochrome c (0.2 μM) or with combination of the same doses of both compounds in the presence of dATP (1 mM) and then assayed for DEVDase activity. (C) AFP differently affects caspase-3 activation in cell-free cytosolic extracts induced by various doses of cytochrome c. Aliquots of S100 cytosolic extract (25 μg of protein) were treated for 30 min with AFP (10 μM) and various doses of cytochrome c in the presence of dATP (1 mM) and then assayed for DEVDase activity. The mean ±SD of four determinations is shown.

DETAILED DESCRIPTION OF THE INVENTION

The subject of invention provides peptides, and in particular, artificial synthetic multimeric cyclic peptides, capable of regulation of the apoptotic cell death. More specifically, it relates to the original amino acid sequence on the molecule of human alpha-fetoprotein (AFP) or albumin responsible for regulation of apoptosis in tumor cells.

AFP is a tumor-associated fetal glycoprotein displaying a wide range of biological activities, including cell growth regulation, differentiation of immature cells, immunosuppression of activated immune cells, tumor-specific induction of apoptosis and regulation of apoptotic signals mediated by other factors, regulation of gene expression. Recently it was shown that AFP can induce tumor-selective apoptosis via direct or indirect activation of caspase-3 in whole cells and in a cell-free system (Dudich et al., (1999 *J.Eur.Biochem.* 266, 750-761). According to the present invention, the active site of such effects was found in AFP and also in albumin. The peptides forming the active sites were modeled and a large range of synthetic natural and non-natural peptides were screened for their biological activities.

The peptides according to the present invention can be used for inhibition of various types of cell deaths that are dependent on the cytochrome c-mediated caspase cascade activation, for example, apoptosis induced by oxidative stress, drugs, cytokines, Fas-ligand, alpha-fetoprotein. The peptides can be utilized to prevent apoptosis in culturing cells, to increase organ preservation for organ transplantation, to prevent immunological autoimmune disorders and immunodeficiency syndrome induced by viral infection, side cytotoxic effects after chemotherapy and radiation therapy. Also provided are amino acid sequences of the peptides and methods of producing and using the peptides. The most active structures of the peptides are non-natural synthetic peptides having a rigid molecular form like:

The present inventions was undertaken to determine active site of the AFP molecule responsible for triggering of apoptosis in tumor cells by using theoretical and experimental approaches. It was made a hypothesis that the active peptide, modeling the active site, might directly induce apoptosis in whole cells and trigger caspase-3 activation in a cell free system or could modulate apoptotic signals, induced by AFP and/or other apoptotic factors, such as anti-Fas or cytochrome-c. Surprisingly a synthetic cyclic peptide *Cys-Cys-Arg-Gly-Asp-Val-Leu-Asp-Cys* (called hereto as apocyclin-A, SEQ ID NO: 1), modeled a part of the AFP molecule, sharing an authentic homology with several caspases, appeared to be biologically active. A series of parings and substitutions of amino acids in the apocyclin-A sequence was intended to identify the functionally important amino acids. A large number of peptides related to apocyclin-A were also synthesized. All peptides were tested for their ability to affect survival of tumor cells in culture and to affect caspase activation in cell-free cytosolic lysates. The next step of the peptide testing was to study ability of peptides to affect apoptosis induced by AFP, anti-Fas in whole cells and to modulate caspase activation mediated by Cyt c in a cell-free system. It was demonstrated that the 9-mer peptide apocyclin-A corresponding to AFP sequence 251-259 completely abrogated AFP-mediated apoptosis in tumor cells in vitro and significantly modulates Cyt-c and AFP-mediated caspase activation in cell-free cytosolic extracts. More specifically, in a cell-free system, apocyclin-A significantly enhanced low-dose cytochrome c-mediated caspase activation and decreased the high-dose cytochrome c-induced effects.

A shorter 6-mer peptide p25 partially retained this activity in a cell-free system, but not in the whole cells. It was also demonstrated that AFP-derived peptides displayed mutual antagonism in regulating Cyt c-mediated caspase activation in cell extracts. It was observed that 9-mer peptide apocyclin-A moderately supported low-dose Cyt c-mediated effects and significantly inhibited caspase activation triggered by high doses of exogenous or endogenous cytochrome c. These data show that AFP-derived 9-mer peptide apocyclin-A is the minimal part of AFP that is responsible for the specific binding with unknown cytosolic molecules involved in the apoptosis signaling. The defined structure of this peptide and its artificial nature imply that it can be the active component of a new drug which opposes the action of various apoptotic factors in vitro and in vivo. The applications of this peptide include preventing apoptosis in cultured cells, methods to prevent immunological rejection of allogenic transplants and autoimmune reactions, methods to avoid hepatological septic shock and apoptosis induced by cytokine therapy, etc.

The abbreviations for amino acids as used herein are given in the following table:

| Ala | A | Alanine |
|-----|---|---------|
| Asp | D | Aspartic acid |
| Glu | E | Glutamine |
| Arg | R | Arginine |
| Cys | C | Cysteine |
| Val | V | Valine |
| Leu | L | Leucine |
| Gly | G | Glycin |
| Xaa | X | any amino acid |

To find out the minimal part of the AFP molecule that is responsible for apoptosis signaling peptides containing from 6 to 10 residues were produced via F-MOC solid phase chemistry. Similar peptides corresponding to the homologous sequence of human serum albumin (HSA) were also synthesized. All peptides were assessed for their growth regulative activity in whole cells in culture and also tested for their ability to directly affect caspase activation in cell-free cytosolic extracts. Additionally the peptides were assessed for their ability to modulate apoptosis induced by AFP and anti-Fas cytotoxic Mabs CH-11 in whole cells and also to affect cyt c-induced caspase activation in cell-free system. Artificial cyclic peptide *CCRGDVLDC* (the asterisks denote a potential disulfide bond) (SEQ ID NO: 1) containing the Arg-Gly-Asp (RGD) motif corresponding to the 251-259 sequence of human α-fetoprotein (AFP), homologous cyclic peptide with substitution of $Cys_{252}$ to Gly *CGRGDVLDC* (SEQ ID NO: 4) and linear peptide RGDVLD (SEQ ID NO: 2) corresponding to the residues 253-359 were produced via F-MOC solid phase chemistry. The homologous cyclic peptides from the sequence of human serum albumin *CCHGDLLEC* (SEQ ID NO: 5), *CGHGDLLEC* (SEQ ID NO: 6) and the linear peptide HGDLLE (SEQ ID NO: 3) were also synthesized and used as functional controls. It is to be recognized that peptides containing only the sequence RCD differ drastically from those of the present invention.

Multimeric cyclic RGD-containing peptide from AFP *CCRGDVLDC* (herein apocyclin-A, SEQ ID NO:1) is able to abrogate apoptosis in tumor cells in vitro. It was demonstrated, that apocyclin-A completely cancelled AFP-induced apoptosis in human myeloblastoma U937 cells and significantly inhibits anti-Fas-mediated cell death. Further, the ability of AFP-derived peptides apocyclin-A and linear 6-mer peptide RGDVLD (SEQ ID NO: 2) to affect caspase activation induced by Cyt c and AFP in a cell-free system has been assessed. It was found that apocyclin-A notably enhanced dATP-dependent caspase activation induced by low doses of endogenous or exogenous Cyt c and practically completely abrogated caspase activation induced by high apoptotically active doses of Cyt c. It was also demonstrated that apocyclin-A cancelled AFP-induced Cyt c/dATP-dependent caspase-3 activation in a cell-free cytosolic extracts of HepG2 cells. Linear AFP-derived 6-mer peptide RGDVLD (SEQ ID NO: 2) did not revealed any apoptosis-regulating activity in the whole cells, but was able to abrogate Cyt c/AFP-mediated caspase activation in a cell free system.

It is well known and usually employed approach to raise antibodies against certain functional sites of biologically active proteins like receptors to block them. Such antibodies create at their Fab units structures which exactly fit into the receptor site. On the other hand, anti-idiotypic antibodies can be made to fit the first prepared Fab-units. The anti-idiotypic antibody resembles therefore the active site of the receptor (the key in the "lock and key model" of molecular interactions). According to the present invention, AFP and albumin contain a special active site, what fits to the receptors triggering the cell death cycle, and blocks them. Therefore, a certain part of AFP/albumin, found in the present invention, has the structure blocking the triggering site. The anti-idiotypic antibody against the active site of AFP and/or albumin therefore contains the essential structural information of the molecule capable of blocking the cell death receptor. Such 3-D structure can be revealed by a routine X-ray crystallography or by molecular computer modeling from a sequence data.

The main practical result of the present invention is the cyclic peptide from AFP, *CCRGDVLDC* ( SEQ ID NO:1, apocyclin-A), which contains two functional active sites: RGD and DVLD. Both sequences are directly involved in the regulation of caspase activity and apoptosis. RGD-containing proteins or peptides are known to be involved in interaction with integrin molecules and could be employed for inhibition of intracellular contacts affecting thus cell proliferation and apoptosis. Apocyclin-A differs from other RGD-containing peptides by multimeric representation of this site in the cyclised form. This allows enhancing of the total effect by multimeric presentation of the RGD sequence.

The sequence DVLD is located in apocyclin-A just after RGD and represents the well-known cleavage site for caspase-3, -7, and -2. Therefore, it has a structure typical for caspase substrates, DXXD (Garcia-Calvo M., et al. (1998) *J. Biol. Chem.*, 32608-13). In apocyclin-A, this site could bind to the active site of caspase-3 as a peptide substrate. The similar activity could be attributed also to the entire AFP molecule, but this will require conformational change allowing exposure of corresponding site to reveal apoptosis-modulating activity (Semenkova et al., (2003) *Eur. J Biochem.* 270: 276-282).

The ability of the apocyclin-A to inhibit activity of caspase-3 in a cell-free system could be explained by the presence of the substrate-like amino acid sequence, which is capable binding to and blocking the active sites of corresponding caspases. Additionally, DVLD-site of apocyclin-A could selectively facilitate the release of caspase-3 from the apoptosome complex by disturbing an interaction between XIAP and processed caspase-3 similarly to the typical tetrapeptide caspase-3 inhibitor DEVD-cho (Bratton, S. B., et al., (2001) *EMBO J.* 5:998).

The unique nature of apocyclin-A is its cyclic structure, which allows multimeric presentation of the substrate sequence and enhancing of the total effect by the simultaneous interaction with different molecules involved in apoptosis signaling.

The invention is illustrated further below by the non-limiting examples.

EXAMPLE 1

Peptide Synthesis

The peptides were synthesized with a synthesizer Model 430A; Applied Biosystems, Foster City, Calif., USA, according to usual methods of peptide syntheses. The cyclic peptides primarily form spontaneously from linear peptides in water solutions subjected to atmospheric oxygen and were purified from the solution by HPLC with common procedures used for peptides.

1. Cyclic multimeric 9-mer peptide corresponding to the 251-259 amino acid sequence of the human AFP *Cys-*Cys-Arg-Gly-Asp-Val-Leu-Asp-Cys*, *CCRGDVLDC* (SEQ ID NO:1) (the asterisks denote a potential disulfide bond), that will be mentioned herein as apocyclin-A. The second cysteine, Cys252, is capable of formation of the S—S bond between two adjacent cyclic monomeric peptides. Molecular weight of the monomeric cyclic peptide was 983 Da. The apocyclin-A peptide is composed of two or more (less than 5) ring-like 9-mer peptide structures corresponding to the sequence *Cys-*Cys-Arg-Gly-Asp-Val-Leu-Asp-Cys*.

2. Cyclic monomeric peptide *Cys-Gly-Arg-Gly-Asp-Val-Leu-Asp-Cys* (SEQ ID NO:4) (the asterisks denote a potential disulfide bond), corresponding to the 251-259 amino acid sequence of the human AFP with a single amino acid substitution of the Cys252 for Gly to avoid peptide multimerisation by formation of the S—S bonds between the monomers. Molecular weight of the monomeric cyclic 9-mer peptide was 937 Da.
3. Linear peptide from AFP corresponding to the sequence 253-259, Arg-Gly-Asp-Val-Leu-Asp (SEQ ID NO:2) (253-259), Molecular weight of the monomeric cyclic peptide was 674 Da.
4. Cyclic peptide from HAS (human serum albumin) *Cys-Cys-His-Gly-Asp-Leu-Leu-Glu-Cys*, *CCHGDLLEC* (SEQ ID NO: 5)(M.wt: 992);
5. Cyclic peptide from HSA *Cys-Gly-His-Gly-Asp-Leu-Leu-Glu-Cys*, CGHGDLLEC (SEQ ID NO:6) (M.wt: 946). In this peptide Cys252 is substituted for Gly.
6. Linear peptide from HSA p26: His-Gly-Asp-Leu-Leu-Glu, HGDLLE (SEQ ID NO:3) (M.wt:683).

Reagents

Fluorogenic peptide substrates DEVD-AMC and LEHD-AFC were from Alexis Biochemicals (San Diego, USA). Bovine heart cytochrom c (Cyt c), adenylic nucleotide thriphosphate (dATP) and other reagents were obtained from Sigma Chemical Co. Human AFP was isolated from the cord serum using ion-exchange, affinity, and gel-filtration chromatography as described in (Dudich et al., (1999) *Biochemistry*, 38: 10406-10414). AFP purity was established by PAGE and Rocket electrophoresis with monospecific antibodies against human AFP and adult serum proteins and was shown to be not less than 99.8%.

Preparation of Cell-Free Extracts

HepG2, human hepatocarcinoma cells and human monoblastoma cell line U937 originated from American Type Culture Collection. Cell extracts were prepared by lysing cells in a hypotonic extraction buffer. To obtain the cytosolic S-100 fraction, the cell lysate was centrifuged for 1 h at 100,000×g. Extracts were either used immediately or frozen at −70° C. for later use.

Cell-Free Reactions

Cell-free reactions were typically set up in 13-μl reaction volumes. Apoptosis was induced by addition of various doses of bovine heart cytochrom c and/or purified human AFP in the presence of 1 mM dATP. For 13-μl scale reactions, 10 μl of cell extract (~2-4 mg/ml, as determined by the Bradford assay) were supplemented with 1 μl of dATP, 1 μl of Cyt c and/or AFP solutions in reaction buffer to receive necessary final concentration of reagents. To assess activity of peptides, various doses of peptides being dissolved in the reaction buffer together with 1 mM dATP were added to the cell extracts. To determine ability of the peptides to modulate apoptotic effects of Cyt c and AFP, peptides were added to extracts 10 min before cytochrome c or AFP. Control samples were incubated with the equal volume of the buffer (3 μl) without reagent addition. To initiate apoptosis, extracts were incubated at 37° C. for 40 min.

Determination of Caspase Activity

At the end of a caspase activation reaction, extract aliquots (5 μl) were supplemented with fluorogenic substrate DEVD-AMC (3 mM) and then incubated for definite time intervals (0.5-1 h) at 37° C. Reactions were terminated by dilution with addition of 2.0 ml of ice-cold 0.2 mM sodium phosphate buffer, pH 7.5, followed by a measurement of fluorescence with a Perkin Elmer MPF-44A ($\lambda_{exc}$=365 nm and $\lambda_{em}$=440 nm) fluorometer. For each sample, the fluorescence intensity was normalized in the respect of cytosolic protein concentration. Caspase activation was presented as the ratio between the normalized fluorescence intensity of the sample and the corresponding value measured with a control sample.

Induction of Apoptosis

U937 cells were plated out at a density of 4×10³ cells/well in flat-bottom 96-well plates (Costar) in the complete medium and incubated for 2 h before reagent additions. Then cells were treated for 24 h with various doses of AFP dissolved in PBS and then assessed for proliferation. Cell treatment with cytotoxic IgM anti-Fas antibody CH-11 was performed as described. U937 cells were treated with 50 ng/ml of CH-11 antibodies for 18 h. Cells were left untreated or were treated with reagents for adequate time intervals and for the last 4 h of culture were subjected to their [³H]-thymidine (1 Ci/mmol/well) incorporation. Experimental data were expressed as a percentage of [³H]-thymidine incorporation in triplicate cultures relative to the medium control. Cells, cultivated without additions, were taken as a control.

Assay for Peptide Activity

To assess growth regulative activity of peptides various doses of peptides were added to the cells for 24 h and then the cells were assessed for proliferation, cell viability and DNA-fragmentation. To determine ability of peptides to modulate apoptosis induced by other factors Jurkat cells were treated with 20 ng/ml of CH-11 antibodies without ActD, Raji cells were treated with CH-11 in the Jurkat cells were treated with 20 ng/ml of CH-11 antibodies without ActD, Raji cells were treated with CH-11 in the presence of 0.5 μg/ml of ActD for 18 h. For induction of apoptosis with TNF-α, cells (Jurkat, MCF7 or U937) were treated for 24 h with 25 ng/ml of the cytokine and then were assessed for proliferation or viability as described above. HepG2 cells were pre-washed before TNF addition with fresh medium to remove endogenous growth factors.

EXAMPLE 2

Identification of Caspase-3 Specific RGD-Containing Active Site in Human AFP Responsible for Apoptosis Signaling To determine functionally important amino acids in the AFP molecule we determined the amino acid homology of the sequence of human AFP and caspases-3 and -1 and constructed the structures of peptide analogues of the proposed active site. The following sequences were studied aligned:

```
casp-2  QNKPKMFFIQACRGDETDRGV
                 :::::
casp-1  KDKPKVIIIQACRGDSPGVVW
                 :::::
casp-3  TGKPKLFIIQACRGTELDCGI
                 :::. :::
HuAFP   VLDVAHVHEHCCRGDVLDCLQDGEKIMSYICSQQDTLSNKITECCKLTTLERGQCIIHAE  299
        : :.  ::   ::  ::::.:  :    .  :::  .::..:  :.  :::    ::.  ::    :
HSA     VTDLTKVHTECCHGDLLECADDRADLAKYICENQDSISSKLKECCEKPLLEKSHCIAEVE  294
```

Figure 1:
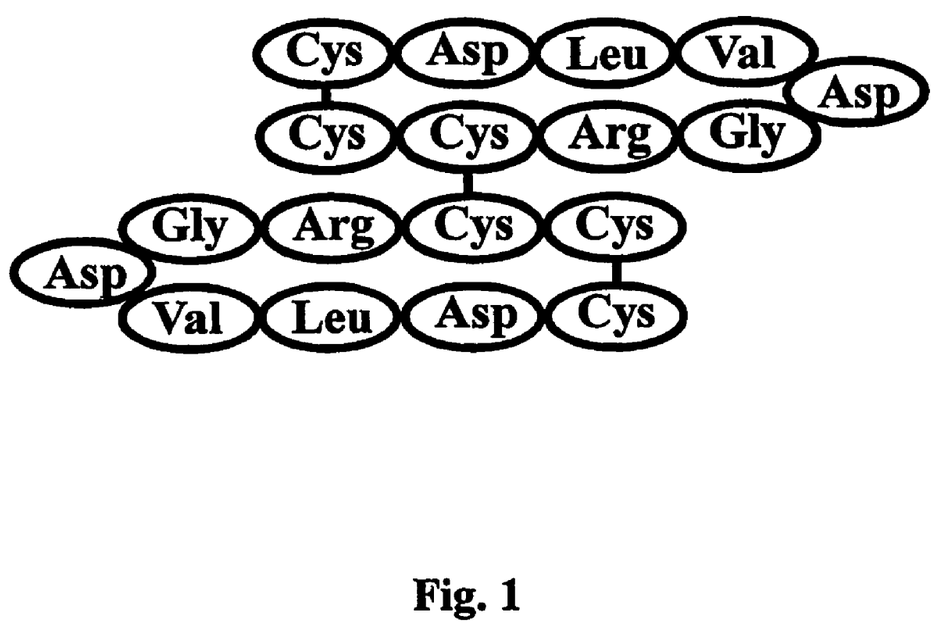
FIG. 1 shows schematic presentation of a biologically active dimeric peptide (the monomer termed here as apocyclin-A; *Cys-Cys-Arg-Gly-Asp-Val-Leu-Asp-Cys* SEQ ID NO:1)

It is seen from the alignment that AFP has certain homology with enzymatic active sites of caspases 1 and 3. Enzymatically active sites of caspases 1 and 2 contain RGD motif that is localized in before catalytically active Cys residue. Effector caspases 3 and 7 have in this place RGT motif, but the positions of Cys residues exactly coincides in AFP molecule and in casp-3 and casp-7. Taking into account that AFP has interchain disulfide bond between $Cys_{252}$ and $Cys_{259}$ (Morinaga, et. al., (1983) *Proc. Natl. Acad. Sci. USA,* 80:4604-4608), we made a hypothesis of localization of the caspase-like active site on the AFP molecule somewhere between residues $Cys_{251}$-$Cys_{259}$. It has to be mentioned that casp-3, -7, and -8 also have RGD motifs, but they are localized at the other that catalytically active positions (Bukley, et al. (1999) *Nature,* 397: 534-539). Free cysteines $Cys_{258}$ in the content of the peptide structure evidently could form interchain disulfide bonds between two adjacent peptides (FIG. 1). To prove the existence of functionally important amino acids in the $Cys_{251}$-$Cys_{259}$ loop in AFP molecule, we constructed the structures of peptide analogues of the proposed active site. For the control, homologous peptides from HSA have been also synthesized.

EXAMPLE 3

Cyclic Peptide From AFP Apocyclin-A Cancels AFP-Induced Apoptosis in U937 Cells

Previous published data demonstrate that AFP from different origins (embryonal or derived from the culture medium of hepatoma cell line HepG2) can induce dose-dependent growth suppression and programmed cell death in various tumor cell lines, characterized by classical features of apoptosis, such as significant growth suppression, cytotoxicity and DNA-fragmentation (Dudich et al., (1998) *Tumor Biol.*

Figure 2:
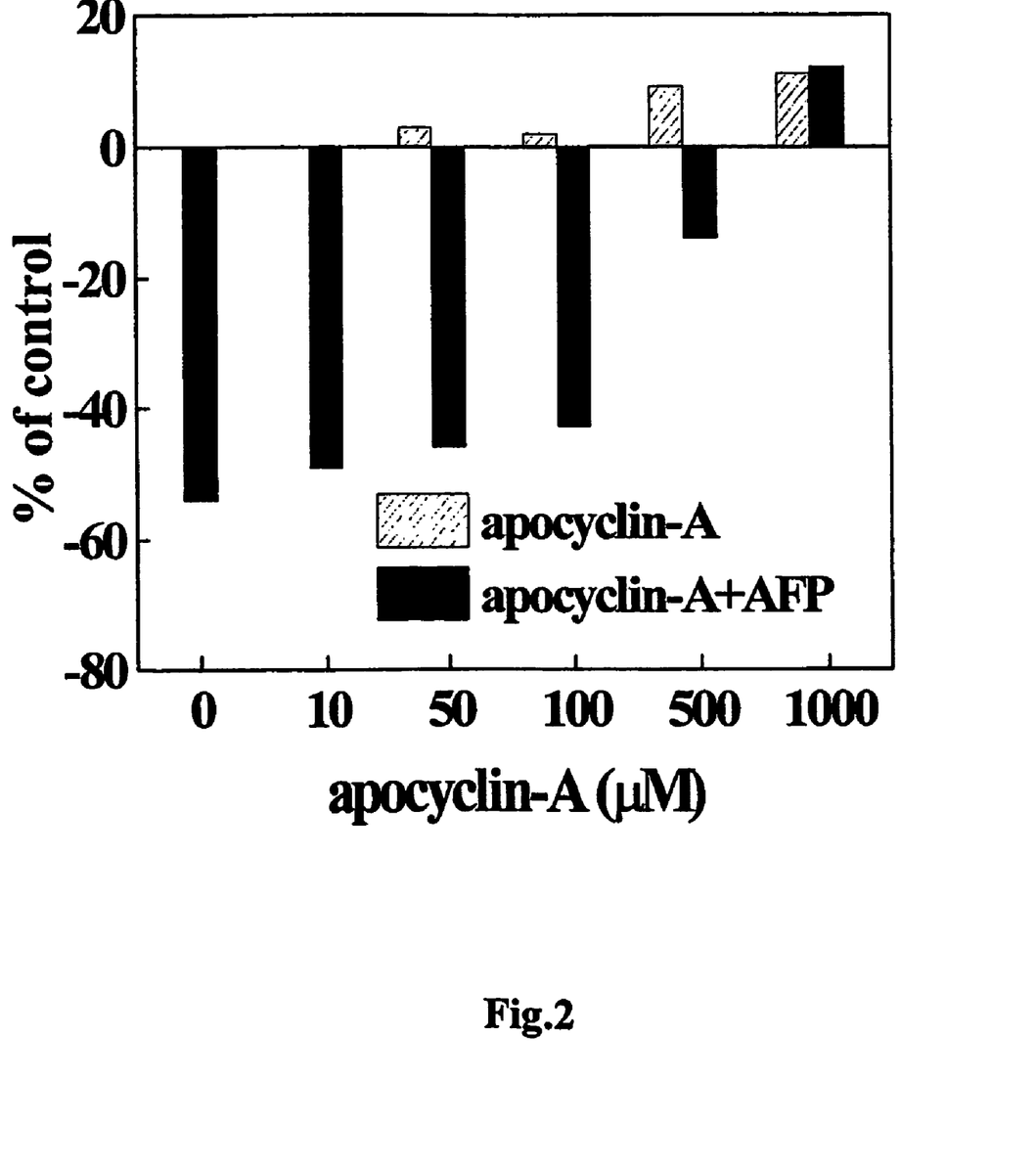
FIG. 2 shows inhibition of AFP-induced apoptosis by the multimeric cyclic 9-mer peptide apocyclin-A (*Cys-Cys-Arg-Gly-Asp-Val-Leu-Asp-Cys* SEQ ID NO:1). U-937 cells in microtiter wells were treated for 15 min with various doses of apocyclin-A and thereafter 3 μM of pure human AFP was added to each well. Cell proliferation was assessed by [$^3$H]-thymidine incorporation assay after 24 h of incubation.

19:30-40). To determine possible localization of the active site on the AFP molecule that is responsible for apoptosis signaling we tested ability of various AFP-derived peptides to block this effect. FIG. 2 demonstrates that AFP-derived peptide apocyclin-A completely abrogates AFP-induced apoptosis in U-937 cells. Moreover, 15-min pre-treatment of U-937 cells with apocyclin-A (1 mM) induced 15% stimulation of proliferation relatively to the medium control. That means that apocyclin-A abrogates also spontaneous apoptosis of the cells during 24-h cultivation.

EXAMPLE 4

Figure 3:
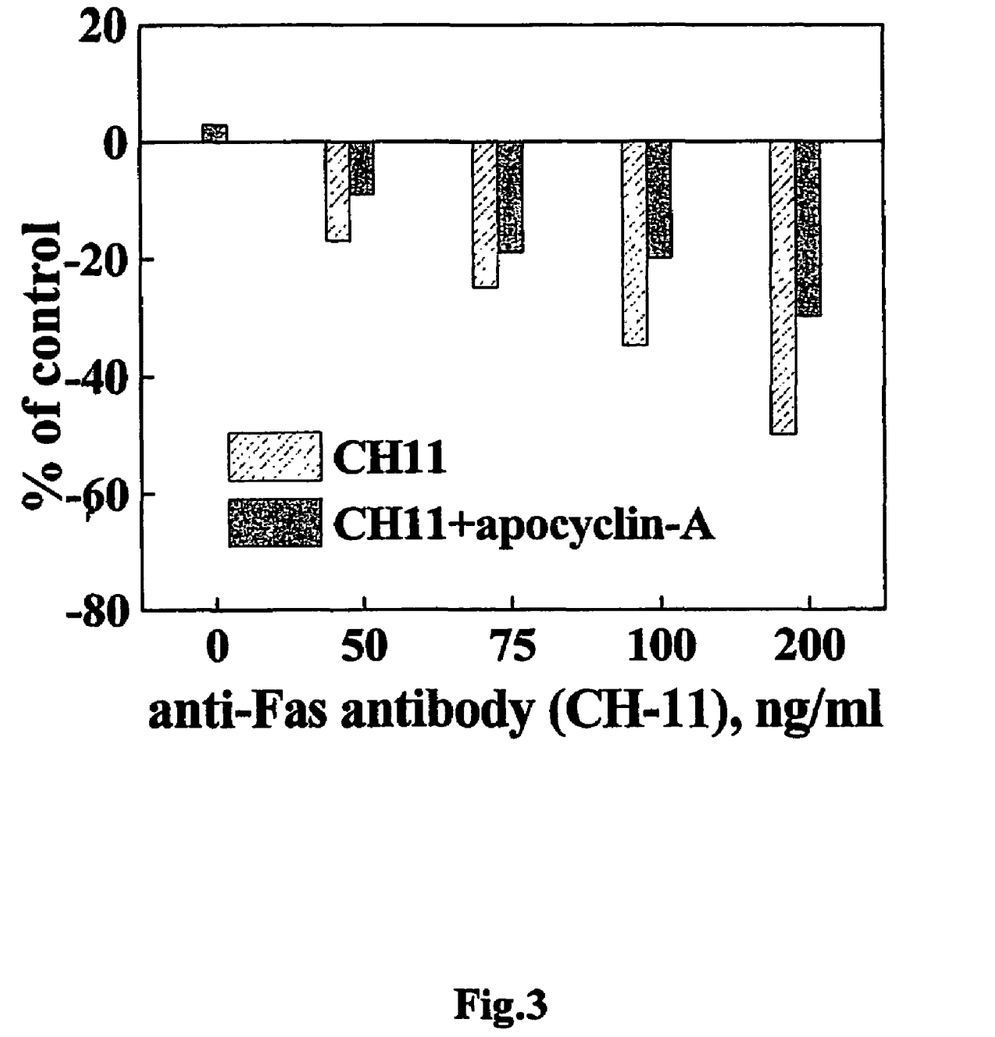
FIG. 3 shows the effect of the cyclic multimeric 9-mer peptide apocyclin-A (*Cys-Cys-Arg-Gly-Asp-Val-Leu-Asp-Cys* SEQ ID NO:1) on the apoptosis induced in U-937 cells by cytotoxic anti-Fas monoclonal antibodies CH-11. Cells were treated for 15 min with 500 μM apocyclin-A and thereafter various doses of cytotoxic anti-Fas Mabs CH-11 (Immunotech Ltd) were added to each well. Cell proliferation was assessed by the [$^3$H]-thymidine incorporation assay after 16 h of incubation.

Apocyclin-A Significantly Inhibits Anti-Fas-Induced Apoptosis In U-937 Cell Line To test AFP-specificity, we tested whether apocyclin-A could affect apoptosis induced by other factors. The apoptosis was induced in U-937 cells by various doses of cytotoxic IgM anti-Fas monoclonal antibodies CH-11. FIG. 3 demonstrates that 0.5 mM apocyclin-A significantly inhibited anti-Fas-mediated apoptosis by abrogation of about 50% of the total effect. Enhance of the apocyclin-A concentration up to 1 mM induced more significant inhibition of the anti-Fas-induced apoptosis. It is known that intracellular pathways engaged in various types of apoptosis are common for majority of apoptotic factors. Our data indicated that apocyclin-A counteracts with AFP- and Fas-dependent pathways of apoptosis signaling by interaction with certain common receptor that is engaged by the both factors to signal apoptosis.

EXAMPLE 5

Determination of the Functionally Important Amino Acids in the Active Site of the AFP Molecule:

a) AFP-Derived Peptides

Figure 4:
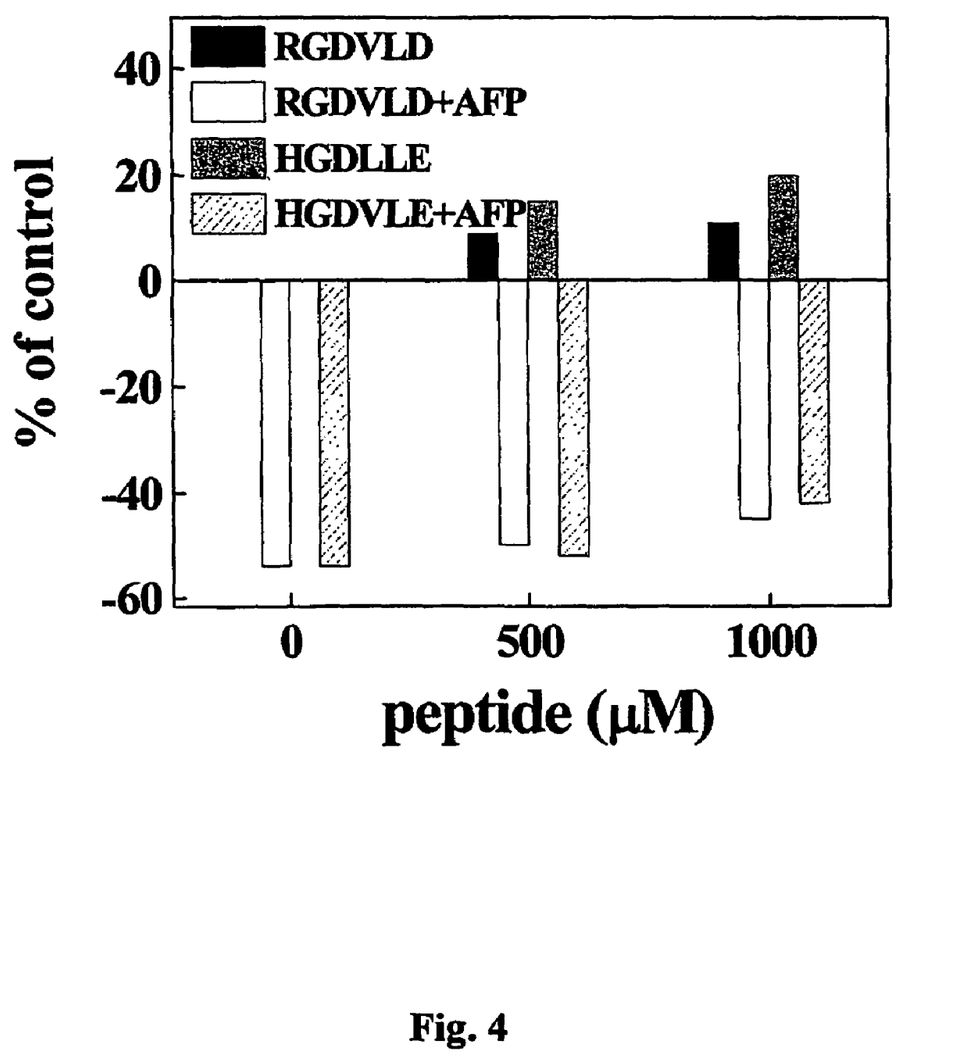
FIG. 4 shows effects of linear 6-mer peptides Arg-Gly-Asp-Val-Leu-Asp (RGDVLD SEQ ID NO:2) and His-Gly-Asp-Leu-Leu-Glu (HGDLLE SEQ ID NO:3) on the AFP-mediated growth suppression of U-937 cells. The cells were treated for 15 with various doses of the peptides and thereafter 3 μM pure human AFP was added to each well. Cell proliferation was assessed by the [$^3$H]-thymidine incorporation assay after 24 h of incubation.

Cyclic peptide *CGRGDVLDC* (SEQ ID NO: 4) with substitution of $Cys_{252}$ to Gly and 6-mer peptide RGDVLD (SEQ ID NO:2) were designed to determine functionally important amino acids in the sequence of the functional active site that is responsible for apoptosis signaling. FIG. 4 demonstrates the effect of—*CGRGDVLDC* (SEQ ID NO:4) on the AFP-mediated apoptosis in U-937 cells. This peptide failed to abrogate AFP-mediated cytotoxicity. The same results were obtained for RGDVLD (SEQ ID NO: 2) (FIG. 4). These data indicate that $Cys_{252}$ is functionally important amino_acid and its substitution to Gly completely abrogates ability of the peptide to interact with apoptotic activity of the entire AFP molecule. The shorter peptide, RGDVLD (SEQ ID NO: 2), was also incapable of regulation of the AFP-mediated apoptosis, showing necessity of cyclic structure for formation of apoptotic active site.

b) HSA-Derived Peptides

Figure 5:
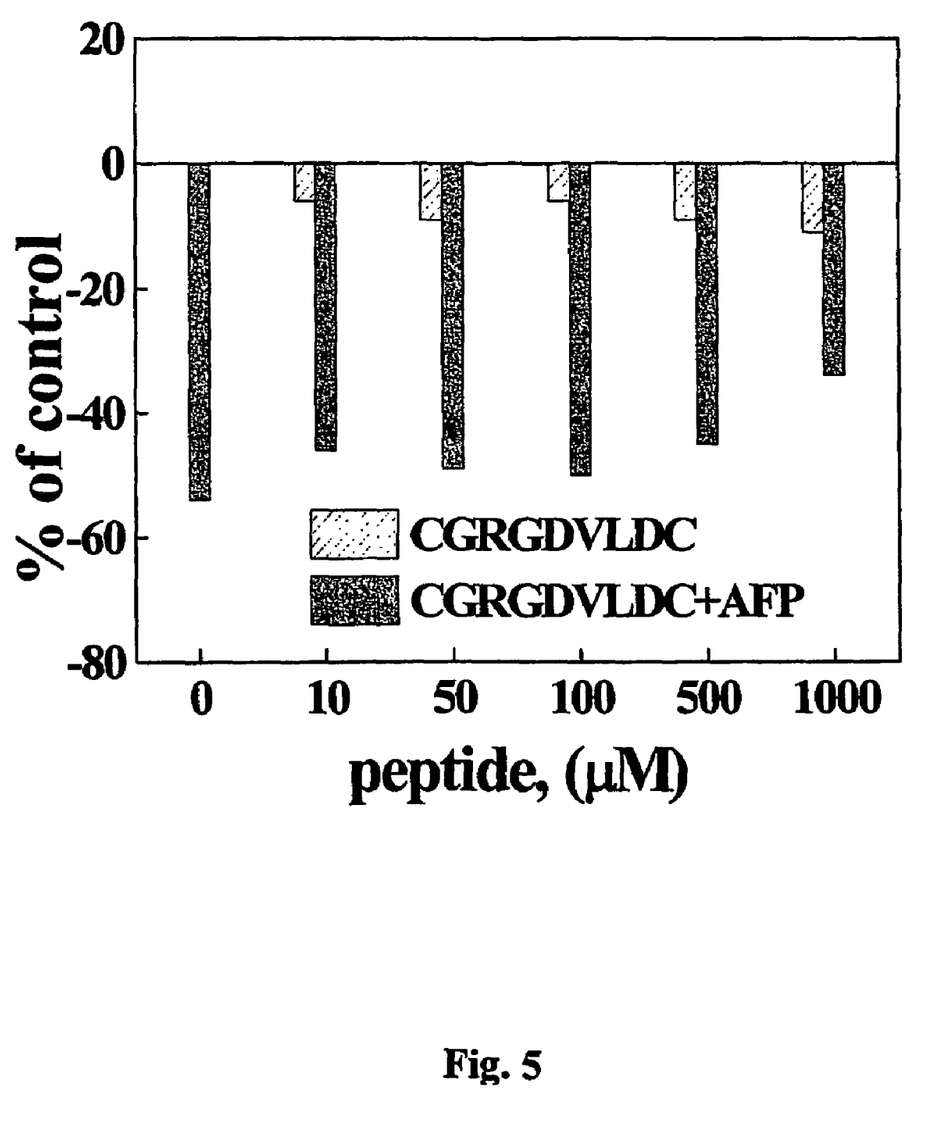
FIG. 5 shows the effect of the cyclic monomeric 9-mer peptide *Cys-Gly-Arg-Gly-Asp-Val-Leu-Asp-Cys* (*CGRGDVLDC* SEQ ID NO:4) on AFP-mediated growth suppression of the human myeloblastoma cell line U-937. The cells were treated for 15 min with various doses of the peptide and thereafter 3 μM pure human AFP was added to each well. Cell proliferation was assessed by the [$^3$H]-thymidine incorporation assay after 24 h of incubation.
Figure 6:
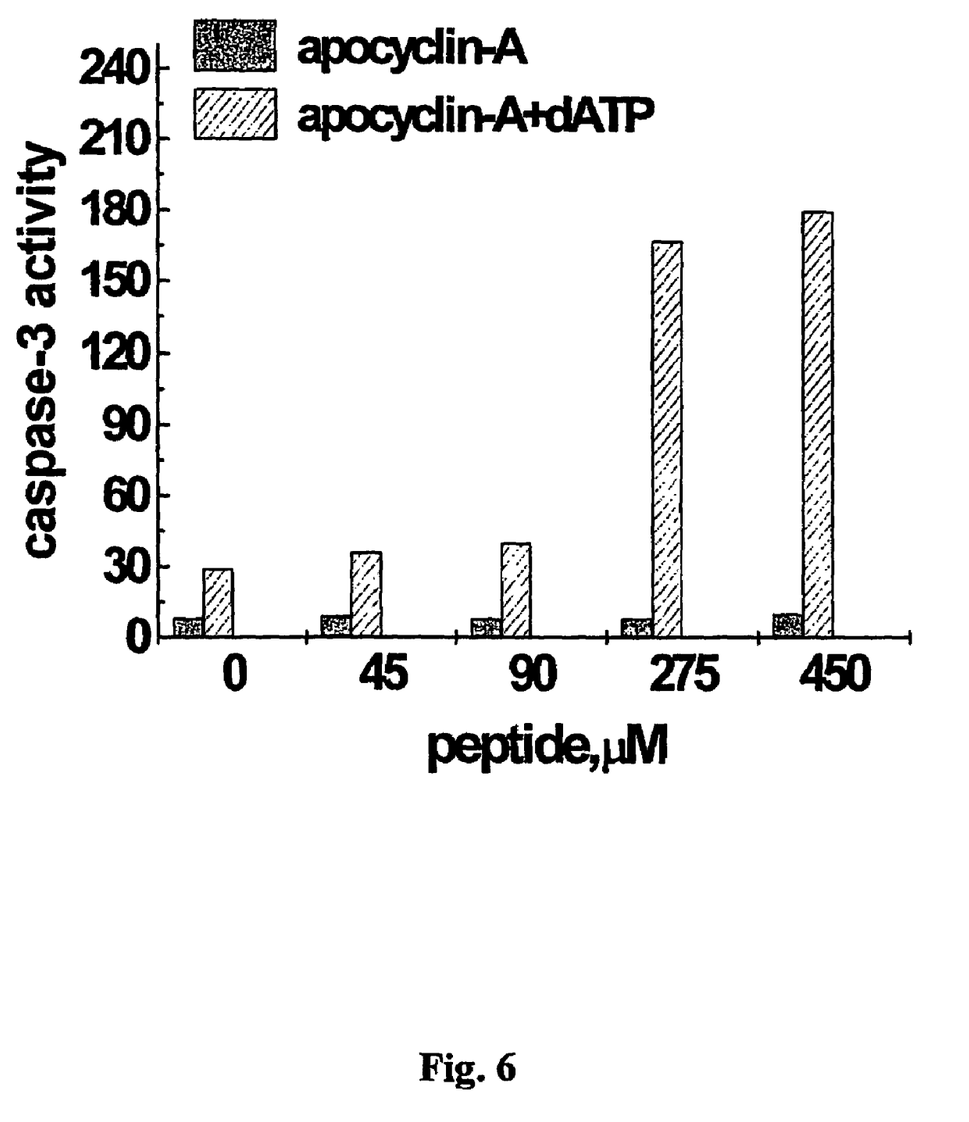
FIG. 6 shows that cyclic 9-mer peptide apocyclin-A (*CCRGDVLDC* SEQ ID NO:1) enhances ATP-dependent pro-caspase-3 activation in a cell-free cytosolic extracts induced by low doses of endogenous Cyt c. Cell extracts from U937 cells were incubated for 40 min with various doses of apocyclin-A and 1 mM of dATP. Extracts incubated without additions were taken as a control. Caspase-3 activation was assessed by cleavage of fluorogenic substrate DEVD-AFC.

Albumin is known to share authentic homology with AFP (Morinaga, et al., *Proc. Natl. Acad. Sci. USA*, 80:4604-4608). There was also found a homology in the region of proposed active site that was modeled by peptide apocyclin-A. We designed following peptides from HSA sequence: cyclic peptides *CCHGDLLEC* (SEQ ID NO: 5), *CGHGDLLEC* (SEQ ID NO:6) (with a single constitution of Cys to Gly) and linear 6-mer peptide HGDLLE (SEQ ID NO:3). We also tested the ability of these peptides to affect AFP-induced apoptosis in whole cells similarly as described above (Table 1). FIG. 5 demonstrates that *CCHGDLLEC* (SEQ ID NO:5) have similar to apocyclin-A activity to abrogate AFP-mediated apoptosis in U-937 cells. HGDLLE (SEQ IDN NO: 3) and *CGHGDLLEC* (SEQ ID NO: 6) did not affect cell response to AFP.

TABLE 1

Effects of AFP-derived and HSA-derived peptides on the cell growth and AFP-induced apoptosis in U-937 cells

| Origin | Sequence | [1]Effect on the cell growth (% of control) | Ability to affect AFP-induced apoptosis |
|---|---|---|---|
| AFP (apocyclin-A) | *CCRGDVLDC* | +12 | Complete abrogation |
| AFP | CGRGDVLDC | −12 | no effect |
| AFP | RGDVLD | +10 | no effect |
| HSA | *CCHGDLLEC* | +18 | Complete abrogation |
| HSA | HGDLLE | +20 | no effect |

*Cyclic peptides
[1]Direct effect of peptides in dose 1 mM on the U-937 cell proliferation in % of control without additions.

EXAMPLE 6

Figure 8:
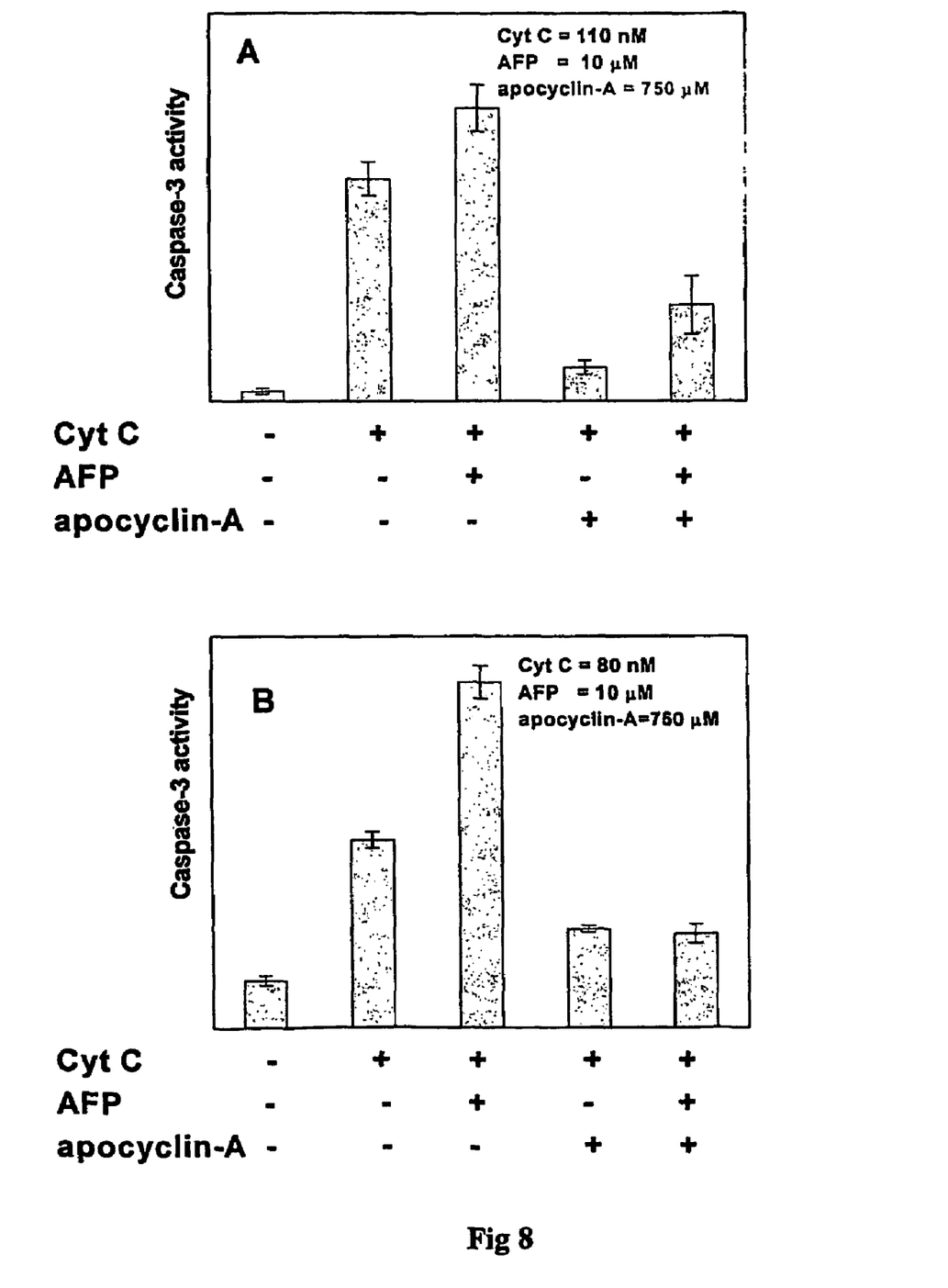
FIG. 8 shows the effects of peptides apocyclin-A *CCRGDVLDC* (SEQ ID NO:1), CGRGDVLDC (SEQ ID NO:4), *CCHGDLLEC* (SEQ ID NO:5), RGDVLD (SEQ ID NO:2) and HGDLLE (SEQ ID NO:3) on the dATP-dependent Cyt c-induced caspase activation in cell-free cytosolic extracts of HepG2 cells at high dose (165 nM) of endogenous cytochrome c (A) and low dose (110 nM) of endogenous cytochrome c (B). Peptides in the concentration of 750 μM were added to the cell extracts 15 min before the cytochrome c addition. Caspase activation was monitored by the cleavage of caspase-3-specific fluorogenic substrate DEVD-AMC.

Apocyclin-A Synergizes With Low Suboptimal Doses of Endogenous Cytochrome c to Induce Caspase Activation in a Cell-Free System To determine whether apocyclin-A could operate similarly to the entire AFP molecule to support caspase activation in a cell-free system, we established the same cell-free system, as described above, but instead of AFP the cyclic peptide apocyclin-A have been used. FIG. 8 demonstrates that apocyclin-A synergistically enhanced the total caspase-3 activity in a cell-free system in the presence of the low suboptimal doses of endogenous cytochrome c and dATP. Without dATP addition apocyclin-A was unable to induce DEVD-ase activity in the same experimental conditions. The same effect was observed for the entire AFP in the "silent" cell-free extracts. These data shows that we were able to identify the active site of AFP and albumin responsible for their apoptosis-promoting activity.

EXAMPLE 7

Figure 7:
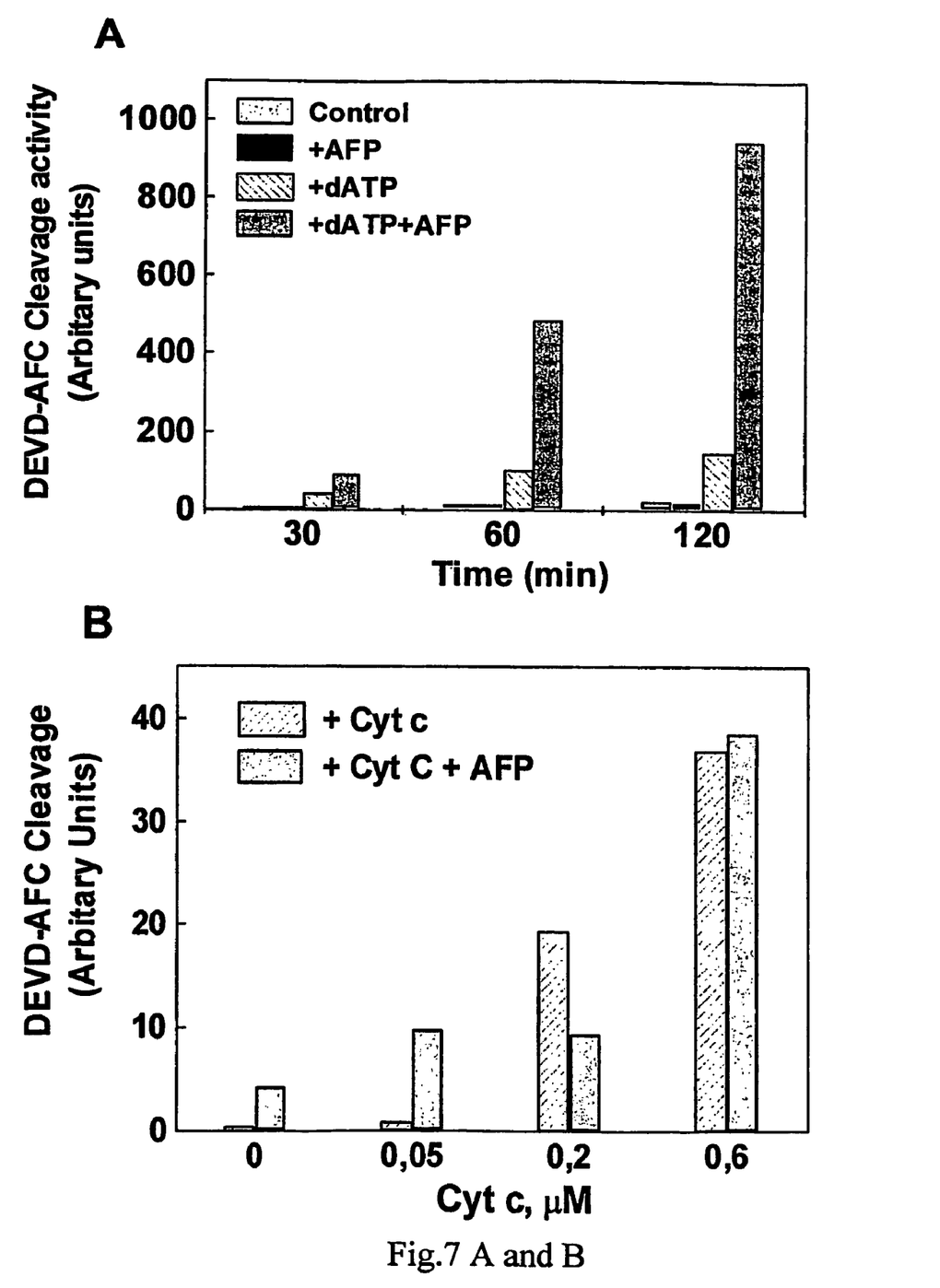

AFP Synergizes With Suboptimal Doses of Cytochrome c and dATP to Induce Caspase-3 Activation in Cytosolic Cell Extracts We have tested further the ability of AFP to induce caspase activity in a cell-free system. Addition of AFP to the S100 cytosolic extract triggered dATP-dependent induction of caspase-3-specific DEVDase activity, which progressively increased for at least 2 h (FIG. 7A). As a control, the equivalent amount of human serum albumin (HSA) was added into the same cell-free system and showed no effect at the level of the DEVDase activity. A low degree of DEVDase activity was also caused by dATP alone and was evidently due to the presence of a small amount of endogenous cyt-c in the preparations. In the absence of dATP, AFP did not induce any caspase activation at all. To determine, whether AFP can directly induce caspase activation in cytosolic cell extracts, or it requires presence of a basal level of cyt-c, we examined DEVDase cleavage activity after addition of exogenous cyt-c to the "silent" cytosolic extracts with undetectable level of endogenous cytochrome c. FIG. 7B shows that no DEVDase activity was detected in this type of cytosolic lysates even after two hours of treatment in the presence of dATP and low suboptimal dose of cyt-c. However, addition of AFP (7 μM) in the same reaction system triggered the process of caspase activation, which progressively increased in a time-dependent manner (FIG. 7B).

EXAMPLE 8

Abrogation of the Cyt c/AFP-Mediated Caspase Activation in a Cell-Free System By Apopcyclin-A FIG. 8 shows that the effects of apocyclin-A on the caspase-3 activation was mediated by various doses of cytochrome c and AFP. High dose of the peptide (750 μM) significantly (50-70%) inhibited caspase activation induced by high doses of endogenous cytochrome c (FIG. 8A). The combined treatment of cytosolic fraction with cytochrome c/AFP resulted in a significant enhance of the total DEVDase activity (FIGS. 8, A and B). Addition of apocyclin-A inhibited Cyt c/AFP-mediated caspase activation by 60-80%. These data indicate that apocyclin-A operates in a cell-free system in the manner opposite to the entire AFP molecule, by abrogation of the total caspase-activation effect induced by cyt c alone or in composition with AFP. Therefore, apocyclin-A represents the sequence on the AFP molecule that is responsible for its apoptotic activity and for the interaction with the members of the apoptosome assembly.

EXAMPLE 9

Figure 9:
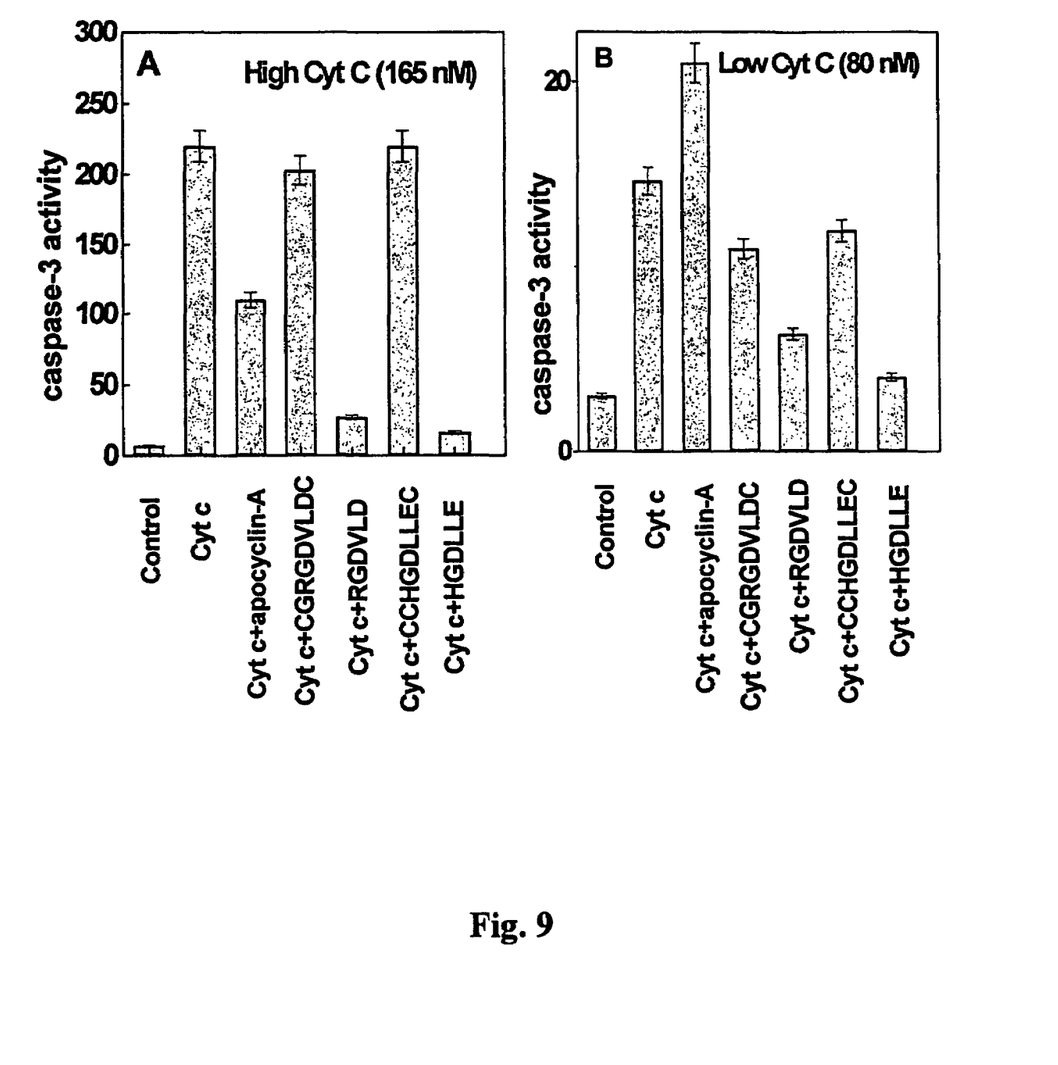
FIG. 9 shows that cyclic multimeric nonapeptide apocyclin-A (*CCRGDVLDC* (SEQ ID NO: 1)) abrogates cytochrome c/AFP -mediated caspase-3 activation in a cell-free system. Aliquotes of HepG2-derived cytosolic extract were pretreated for 15 min with 750 μM of apocyclin-A and then treated for 40 min with 10M of AFP and/or 110 nM (A) or 80 nM (B) of cytochrome c in the presence of 1 mM of dATP. Caspase activation was monitored by the cleavage of specific caspase-3 fluorogenic substrate DEVD-AMC.

Effects of AFP-Derived and HSA-Derived Peptides on the dA TP-Dependent Cyt c-Mediated Caspase Activation in Cell-Free Cytosolic Extracts To test ability of various peptides to affect caspase activation induced by exogenous cytochrome c in cell free system, we used cytosolic cell extracts of HepG2 cells. Aliquots of cell extracts were pre-treated with 750 μM of peptides for 15 min and thereafter various doses of cytochrome c was introduced in the reaction mixture to induce caspase activation. Control extracts were incubated with dATP without peptides and cytochrome c but it did not reveal any caspase activity. It is seen from FIG. 9 A that the peptides from AFP, 9-mer peptide apocyclin-A and 6-mer peptide RGDVLD as well as 6-mer peptide from HSA, HGDLLE induced significant inhibition of high dose cytochrome c-mediated caspase activation. On the other hand, cyclic monomeric 9-mer peptide with a single amino acid substitution *CGRGDVLDC*, as well as cyclic multimeric peptide from HSA *CCHGDLLEC*, showed no activity to inhibit apoptosis either in whole cells or in a cell-free system. Hence, the most potential peptide apocyclin-A mimics the active site of AFP which is responsible for the apoptosis signaling. Distinctly different effect was obtained for the low dose cytochrome c-induced caspase activation. FIG. 9B shows that apocyclin-A produced the same stimulation as full-length AFP molecule at low dose cytochrome c-induced caspase activation. Peptides *CGRGDVLDC* and *CCHGDLLEC* had no effect on the low-dose cytochrome c activity, but peptides RGDVLD and HGDLLE demonstrated significant abrogation of the cytochrome c-induced caspase activation.

Table 2 summarizes experimental data characterizing activity of peptides in cell-free cytosolic extracts.

TABLE 2

Modulation of the Cyt c-mediated DEVDase activity by various peptides in a cell free system

| Sequence | Effect on the high dose Cyt c-induced caspase activation | Ability to affect AFP-induced Cyt c-dependent caspase activation | Effect on the low dose Cyt c-induced caspase activation |
| --- | --- | --- | --- |
| *CCRGDVLDC* | 50-80% abrogation | 70-80% abrogation | 30% stimulation |
| CGRGDVLDC | no effect | no effect | no effect |
| RGDVLD | 80% abrogation | no effect | 30-50% abrogation |
| *CCHGDLLEC* | no effect | no effect | no effect |
| HGDLLE | 90% abrogation | no effect | 70% abrogation |
| Entire AFP | 80% abrogation | — | 50% stimulation |

*Cyclic peptides

EXAMPLE 10

Preparation of Anti-Idiotypic Antibodies Against the Biologically Active Site of AFP BALB/cA mice were used for immunization, cell fusion and production of ascites fluid. Twenty mice were immunized each with a highly purified human AFP (40 μg) emulsified with complete Freund's adjuvant. The mice were boosted at 2-week intervals with the same amount of AFP emulsified in incomplete Freund's adjuvant. The mice with the highest response against human AFP were selected and 80 μg of AFP in 100 μl of AFP solution involving 50 μl of Freund's incomplete adjuvant was intravenously injected into their tails. Three days later spleen cells were prepared and mixed with mouse myeloma NS-1 cells followed by the treatment with PEG in the KC medium containing FCS. The fusion cells were grown in HAT medium containing FCS followed by cultivation in HT medium. The hybridomas were tested for their production of antibodies with a TR-FIA assay involving rabbit polyclonal antibody as an immobilized capturing antibody and an Eu-labeled anti-human antibody as the monitoring antibody (for technical details and reagents, see the publication Peuravuori, H and Korpela, T. et al. Clin. Chem.1993, 39, pp. 847-848). Among the antibody producing clones, those which were not sensitive to addition of peptide *CCRGDVLDC* (SEQ ID NO: 1) and its cyclic forms were discarded. Clones showing a good response were grown enough to be introduced for ascites fluid production in mice. The ascites fluid was prepared and anti-AFP monoclonal antibodies were purified from it. The purified antibodies were subjected to proteolysis to obtain pure Fab fragments from selected clones by commonly known methods (for techniques, see paper by Muronetz and Korpela, J. Chromatogr. 2003, 790, pp. 53-66). The Fab-protein was subjected to a similar process as AFP, described above, to obtain monospecific antibodies against the Fab fragments. Those anti-idiotypic antibodies against AFP active site were screened out from the clones by their sensitivity to the active site peptides of AFP. The anti-idiotypic antibody against the active site of human albumin at the sequence position 246-254 could be made essentially by the same techniques as against AFP described above.

The invention claimed is:

1. An isolated cyclic peptide consisting of an amino acid sequence CCRGDVLDC (SEQ ID NO:1). said sequence corresponding to apoptotically active site of human alpha-fetoprotein localized at amino acid residues 251-259 of said fetoprotein, said peptide having its cyclic structure through disulfide bonds between the first cysteine residue and the ninth cysteine residue and said peptide having a capability to regulate apoptotic cell death.

2. A method for suppressing apoptotic regulatory pathways in human and animal cells by treating the cells with peptide according to claim 1 for an appropriate period of time.

3. A method to inhibit cell apoptosis by using the peptide of claim 1.

4. The method according to claim 2, wherein the cells are cultured for scientific or technical purposes.

5. The peptide according to claim 1, wherein the structure has an ability to bind into an antibody prepared against the molecular recognition site of a Fab-fragment or said anti-idiotypic antibody.

6. An isolated cyclic peptide, wherein the peptide is a dimer of SEQ ID NO: 1 formed via disulfide bond between free cysteines, found in the second positional residue of peptide monomers of SEQ ID NO: 1.

7. The method of claim 3, wherein the apoptosis is selected from the group consisting of neuronal cell apoptosis non-specific drug-induced apoptosis, and oxidative stress-mediated apoptosis.

* * * * *

UNITED STATES PATENT AND TRADEMARK OFFICE
CERTIFICATE OF CORRECTION

| | | |
|---|---|---|
| PATENT NO. | : 7,446,095 B2 | Page 1 of 1 |
| APPLICATION NO. | : 10/530779 | |
| DATED | : November 4, 2008 | |
| INVENTOR(S) | : Elena Ivanovna Dudich et al. | |

It is certified that error appears in the above-identified patent and that said Letters Patent is hereby corrected as shown below:

Title Page, Item (76) Inventors, third inventor name should read --Eduard Borisovitch Tatulov--.

Signed and Sealed this

Seventh Day of February, 2012

David J. Kappos
*Director of the United States Patent and Trademark Office*

SEQUENCE LISTING

<160> NUMBER OF SEQ ID NOS: 6

<210> SEQ ID NO 1
<211> LENGTH: 9
<212> TYPE: PRT
<213> ORGANISM: artificial
<220> FEATURE:
<223> OTHER INFORMATION: peptide sequence localized at aa residues
      251-259 of human alpha-fetoprotein
<220> FEATURE:
<221> NAME/KEY: PEPTIDE
<222> LOCATION: (1)..(9)
<223> OTHER INFORMATION: peptide sequence called Apocyclin when a
      monomer

<400> SEQUENCE: 1

Cys Cys Arg Gly Asp Val Leu Asp Cys
1               5

<210> SEQ ID NO 2
<211> LENGTH: 6
<212> TYPE: PRT
<213> ORGANISM: artificial
<220> FEATURE:
<223> OTHER INFORMATION: peptide sequence found in  human
      alpha-fetoprotein

<400> SEQUENCE: 2

Arg Gly Asp Val Leu Asp
1               5

<210> SEQ ID NO 3
<211> LENGTH: 6
<212> TYPE: PRT
<213> ORGANISM: artificial
<220> FEATURE:
<223> OTHER INFORMATION: peptide sequence found from human serum
      albumin

<400> SEQUENCE: 3

His Gly Asp Leu Leu Glu
1               5

<210> SEQ ID NO 4
<211> LENGTH: 8
<212> TYPE: PRT
<213> ORGANISM: artificial
<220> FEATURE:
<223> OTHER INFORMATION: peptide sequence modified from a sequence found
      in human alpha-fetoprotein or in human serum albumin

<400> SEQUENCE: 4

Cys Gly Arg Gly Asp Val Leu Asp
1               5

<210> SEQ ID NO 5
<211> LENGTH: 9
<212> TYPE: PRT
<213> ORGANISM: artificial
<220> FEATURE:
<223> OTHER INFORMATION: peptide sequence localized at aa residues
      244-253 of human serum albumin

<400> SEQUENCE: 5

Cys Cys His Gly Asp Leu Leu Glu Cys
1               5

```
<210> SEQ ID NO 6
<211> LENGTH: 9
<212> TYPE: PRT
<213> ORGANISM: artificial
<220> FEATURE:
<223> OTHER INFORMATION: peptide sequence modified of a peptide sequence
      found in human alpha-fetoprotein or in human serum albumin

<400> SEQUENCE: 6

Cys Gly His Gly Asp Leu Leu Glu Cys
1               5
```